United States Patent [19]

Nishimura

[11] Patent Number: 4,705,045

[45] Date of Patent: Nov. 10, 1987

[54] NON-CONTACT TYPE TONOMETER

[75] Inventor: Shinichi Nishimura, Tokyo, Japan

[73] Assignee: Tokyo Kogaku Kikai Kabushiki Kaisha, Tokyo, Japan

[21] Appl. No.: 832,763

[22] Filed: Feb. 25, 1986

[30] Foreign Application Priority Data

Feb. 26, 1985 [JP] Japan .................................. 60-37237

[51] Int. Cl.⁴ .............................................. A61B 3/16
[52] U.S. Cl. .................................................. 128/648
[58] Field of Search ....................... 128/645, 648–652; 366/144, 146, 151, 153

[56] References Cited

U.S. PATENT DOCUMENTS 3,756,073  9/1973  Lavallee et al. ..................... 128/648
3,832,890  9/1974  Grolman et al. ..................... 128/648
4,154,532  5/1979  Emmerich ....................... 356/153 X Primary Examiner—Edward M. Coven
Attorney, Agent, or Firm—Finnegan, Henderson, Farabow, Garrett & Dunner

[57] ABSTRACT

There is disclosed a non-contact type tonometer for measuring intraocular pressure of an eye under test in which a fluid for deforming a cornea, discharged along an optical axis of an alignment optical system toward the cornea in order to deform the cornea. The intraocular pressure is measured based on the measured deformation of the cornea. The alignment optical system comprises a projection optical system which is independently adapted for projecting a pair of target rays for alignment verification toward the cornea; and an alignment verification optical system in which corneal specular reflection rays of the pair of target rays are guided to the objective lens as if the pair of target rays were radiated from the corneal focal point. When an optical axis of the projection optical system is made coincident with the focal point of the cornea and the reflected target images are formed by the objective lens, alignment verification is effected based on duplication of the pair of target images.

14 Claims, 8 Drawing Figures

NON-CONTACT TYPE TONOMETER

FIELD OF THE INVENTION

This invention relates to an alignment verification of a non-contact type non-contact type tonometer. A fluid for a fluid for transfiguring a cornea is discharged along an optical axis of an alignment optical system for observing the eye under test through an alignment verification objective lens. The fluid is ejected toward the cornea in order to deform the cornea and the intraocular pressure is measured based on the monitored deformation of the cornea.

BACKGROUND OF THE INVENTION

Heretofore, non-contact type tonometers of the type disclosed in U.S. Pat. No. 3756073 have been known. In this conventional non-contact type tonometer, fluid for determining a cornea is discharged along an optical axis of an alignment optical system for observing an eye under test, toward the cornea to deform the cornea. The intraocular pressure is measured based on the deformation of the cornea. If the working distance from a discharging end of an orifice to the cornea is incorrect, and the vertex of the cornea is not in alignment with the optical axis of the alignment optical system, errors are produced in the intraocular pressure measurement. Therefore, a non-contact type tonometer of this type is provided with an alignment verification apparatus.

FIG. 8 is a schematic illustration of an alignment verification optical system functioning as the aforementioned alignment verification apparatus. In FIG. 8, 1 denotes a cornea of an eye under test. The alignment verification optical system includes an objective lens 2, a half mirror 3, a reticle plate 4. The objective lens 2 is used for the alignment optical system and disposed opposite a front part of the cornea 1. The objective lens 2 is provided with an orifice tube 5 penetrating therethrough. A target ray is projected on cornea 1 by a projection optical system (not shown). The target ray reflected from the cornea 1 is guided to the objective lens 2 as a corneal specular reflection ray and forms a target image on the reticle plate 4 by the objective lens 2.

A specialist observes the target image formed on the reticle plate 4 and effects the alignment verification in such a manner that the focussing position of the objective lens 2 will be brought to alignment with the center of curvature 1a of the cornea 1. The optical axis of the objective lens 2 will pass the center of curvature 1a of the cornea 1 through the vertex 0 of the cornea 2. Due to the alignment verification, the target image is clearly formed on the reticle plate 4. A part of the corneal specular reflection ray is reflected by the half mirror 3 and guided to a light detector 6. Accordingly, the non-contact type tonometer is capable of measuring the intraocular pressure based on detection signal of the light detector 6. That is, a fluid actuation device is actuated based on the detection signal, fluid is discharged from the orifice tube 5, the cornea 1 is deformed from convexity, through applanation, to concavity, and the intraocular pressure is measured based on the measured deformation.

The conventional non-contact type tonometer, as shown in U.S. Pat. No. 3756073 is constructed such that when an adjustment or verification is required with respect to the distance (working distance) between the cornea 1 of the eye under test and the orifice tube 5, the alignment verification is effected by bringing the focussing position of the objective lens 2 into alignment with the of curvature center 1a of the cornea 1. Accordingly, if the radius of the curvature of the cornea 1 is not constant, the alignment verification is effected such that the working distance is fluctuated to the extent of the difference in the radius of curvature across the cornea, i.e., ($S_1$–S) as shown in FIG. 8. Accordingly, in the conventional non-contact type tonometer, the errors based on the radius of the curvature of the cornea 1 is directly proportional to errors of the alignment verification. This means that a unique error is produced in measurement of intraocular pressure of an eye under test depending on the shape of a particular patient's cornea. Thus, the conventional non-contact type tonometer lacks accuracy of measurement.

Furthermore, since the alignment verification is effected based solely on clarity of the target image, there is involved the problem that it is not easy to confirm whether the target image is clearly formed, and the alignment verification can not be effected promptly.

SUMMARY OF THE INVENTION

The present invention was accomplished in view of the above mentioned problems.

It is therefore a first object of the present invention to provide a non-contact type tonometer, wherein accuracy of measurement of intraocular pressure can be improved extensively.

It is a second object of the invention to provide a non-contact type tonometer, wherein a satisfactory operation is obtainable with respect to the alignment verification.

In order to achieve the above objects, an alignment optical system according to the invention comprises a projection optical system which is independently adapted in addition to the objective lens for projecting a pair of target rays for alignment verification toward the cornea; and an alignment verification optical system in which corneal specular reflection rays of the pair of target rays are guided to the objective lens as if the pair of target rays were radiated from a focul point of the cornea when an optical axis of the projection optical system is brought to be in conformity with the corneal focal point and formed as target images by the objective lens, and alignment is verified based on duplication of the pair of target images.

According to this alignment optical system, when a pair of target rays are projected toward a focal point of a cornea, the corneal specular reflection rays are guided to the objective lens in the form of parallel rays by the objective lens, and a pair of target images are clearly formed in duplication at a predetermined position by the objective lens. Accordingly, the alignment verification can be effected while confirming the duplication of the pair of target images. Thus, when compared with the case in which the alignment verification is effected by means of projecting a target ray to the center of curvature of the cornea, the measurement errors in the optical axis direction based on the radius of curvature of the cornea can be reduced by at least 50%. In addition, verification thereof can be made with ease.

DETAILED DESCRIPTION OF THE EMBODIMENTS

Figure 1:
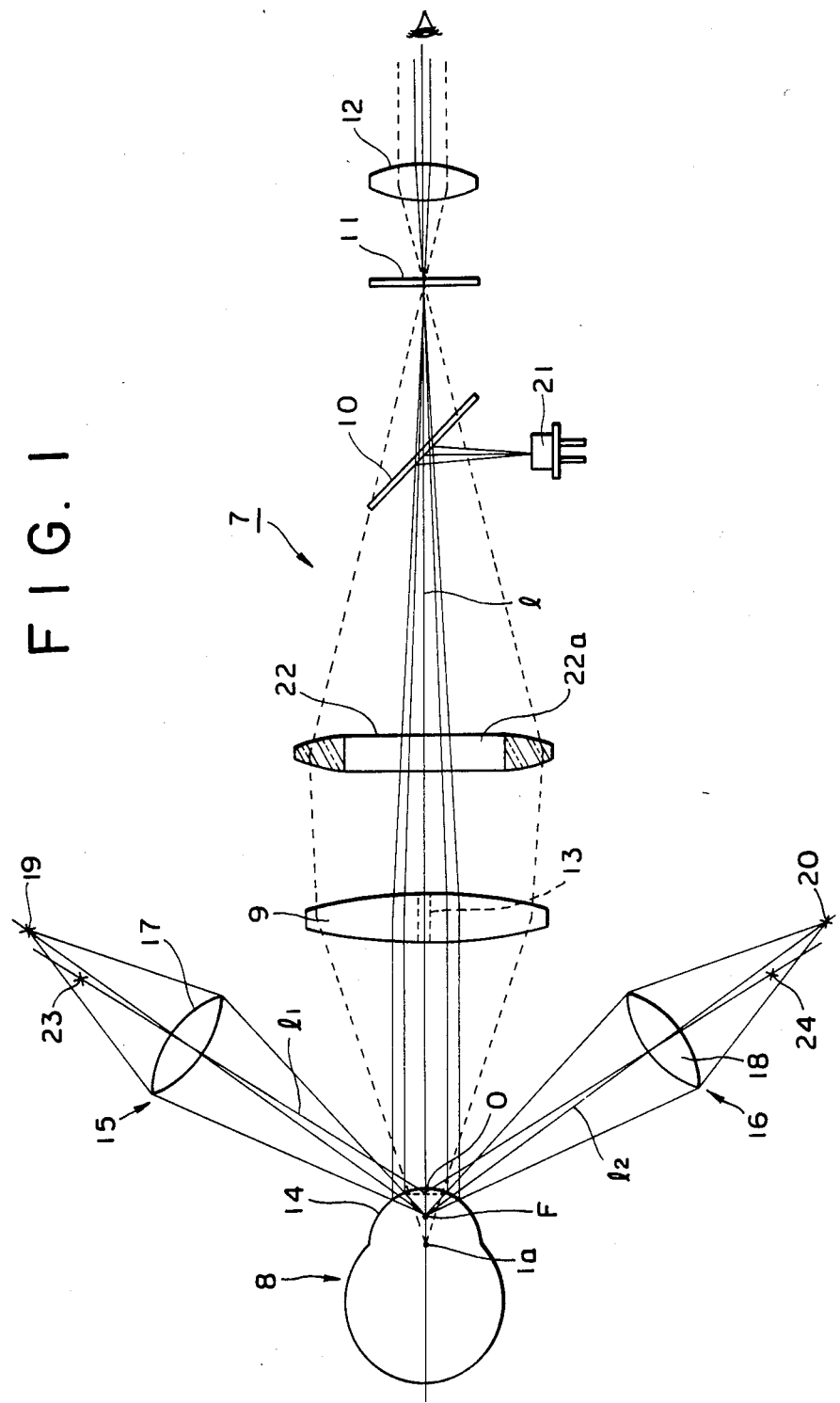
FIG. 1 is a schematic view showing the construction of an alignment optical system of a non-contact type tonometer according to a first embodiment of the present invention.

In FIG. 1, 7 denotes an alignment verification optical system, 1 denotes an optical axis thereof, and 8 denotes an eye under test. The alignment verification optical system 7 includes an objective lens 9, a half mirror 10, a reticle plate 11 and an ocular 12. The objective lens 9 is formed with a through hole 13. The through hole 13 is provided with an orifice tube (not shown) for discharging fluid for conrneal transfiguration toward a cornea 14 of the eye 8 under test.

There are two types of alignment verification; one is of the type in which the so-called working distance in the optical axis from the discharging end of the orifice tube to the vertex 0 of the cornea 14 is verified by moving the objective lens 9. The other is the type in which a target image is moved within a plane perpendicular to the optical axis 1 to bring the optical axis 1 to the center $1a$ of curvature of the cornea 14 through the corneal vertex 0. The foregoing alignment verification is effected by projecting a pair of target rays toward the cornea 14.

15 and 16 denote projection optical systems for projecting the pair of target rays toward the cornea 14. The alignment optical system comprises these projection optical systems 15 and 16, and the alignment verification optical system 7. The projection optical systems 15 and 16 are arranged in symmetric relation with respect to each other with the optical axis 1 disposed therebetween. The projection optical systems 15 and 16 include projection lenses 17 and 18, and target light sources 19 and 20. The pair of target rays become parallel rays radiated from the corneal focal point F based on when the optical axes $1_1$ and $1_2$ of the projection optical systems 15 and 16 are brought to alignment with the focal point F of the cornea, and guided to the objective lens 9 as specular reflection rays of the cornea. The objective lens 9 images the specular reflection rays on the reticle plate 11.

The alignment verification optical system 7 is provided with a light detector 21. The light detector 21 is disposed in conjugate relation with the reticle plate 11 through the half mirror 10. The half mirror 10 reflects a part of the specular reflection rays from the cornea to the light detector 21. The specular reflection rays reflected by the half mirror 10 are imaged on a photosensitive surface of the light detector 21. The light detector 21 generates and transmits an has the function that an alignment alignment completion signal when detecting the predetermined quantity of light indicative of proper alignment. In this embodiment, the alignment verification optical system 7 is provided with an objective lens 22 for forming an anterior portion image of the eye 8 under test during alignment verification. The anterior image is focused at reticle plate 11 by lens 20. The objective lens 22 is formed with a through hole $22a$ at the central portion thereof. The through hole $22a$ the specular reflection rays from the cornea. In FIG. 1, the broken line denotes the imaging bundle of rays of the anterior portion.

Figure 2:
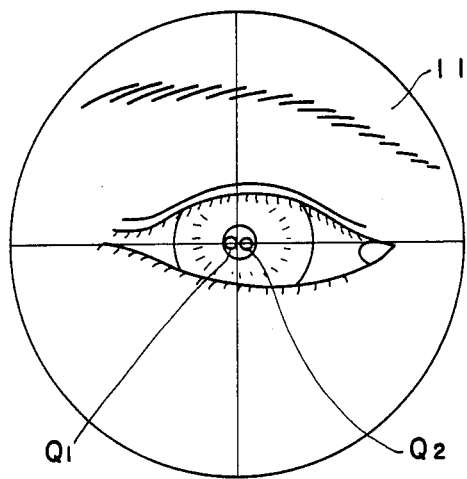
FIG. 2 through FIG. 4 are schematic illustrations illustrating how the alignment verification is effected by using the non-contact type tonometer according to the present invention.
Figure 3:
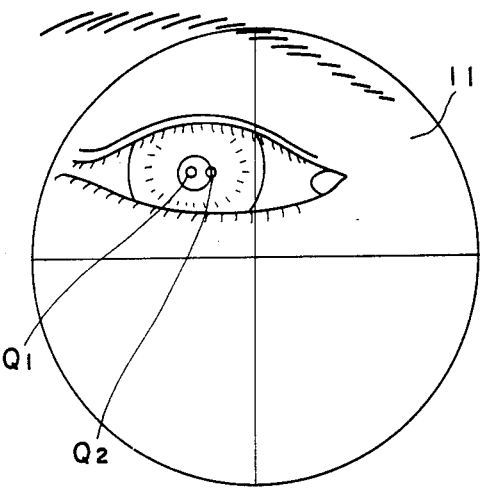
Figure 4:
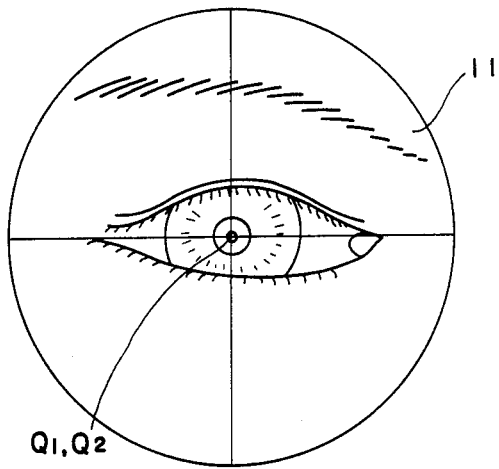

FIG. 2 through FIG. 4 are schematic illustrations showing the anterior portion image and target image formed on the reticle plate 11. In FIGS. 2 through 4, $Q_1$ and $Q_2$ denote the pair of target images. FIG. 2 illustrates the state of the target images where images $Q_1$ and $Q_2$ are separated and not clearly imaged, since the working distance is wrong in the optical axis direction in spite of the fact that the optical axis 1 is in alignment with the vertex 0 of the cornea. On the other hand, FIG. 3 illustrates the state of the target images are images $Q_1$ and $Q_2$ are separated, not clearly imaged, and are offset with respect to a hairline sight formed in of the reticle plate 11, since the working distance is offset in the optical axis direction and the vertex 0 of the cornea is not in alignment with the optical axis 1. FIG. 4 illustrates target images $Q_1$ and $Q_2$ clearly imaged in duplication, as would appear when the vertex 0 of the cornea is in proper alignment with the optical axis 1, and the working distance is properly set in the optical axis direction.

Figure 5:
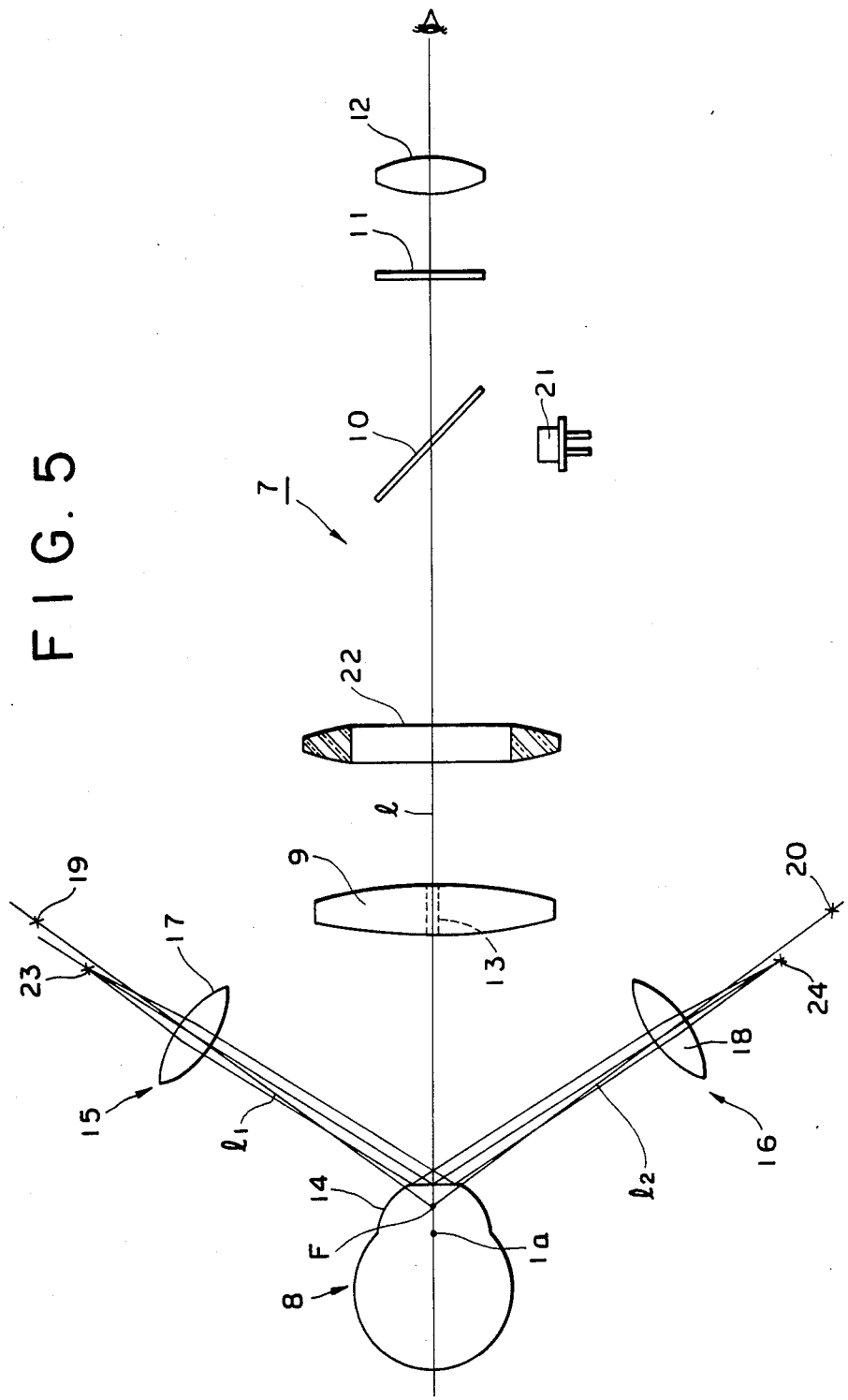
FIG. 5 is a schematic illustration of an optical system illustrating how the detection of the corneal configuration is effected by using the non-contact type tonometer according to the present invention.

When the alignment verification is completed, a fluid actuation apparatus (not shown) is actuated by the light detector 21. At the same time, as shown in FIG. 5, the projection light source 23 of the detection optical system for detecting the deformation of the cornea is activated. When the fluid actuation apparatus is actuated, the fluid is discharged toward the cornea 14 from the orifice tube.

The projection lenses 17 and 18 are commonly used for the detection optical system. The projection light source 23 is located at the focal point of the lens 17. The projection lens 17 projects parallel rays of light toward the cornea 14 at predetermined angles. The projection lens 18 is provided with a light detector 24 at the focal point thereof. The projection lens 18 images the reflected detection rays on the light detector 24. In this manner, the corneal deformation is optoelectrically detected by the light detector 24.

Figure 6:
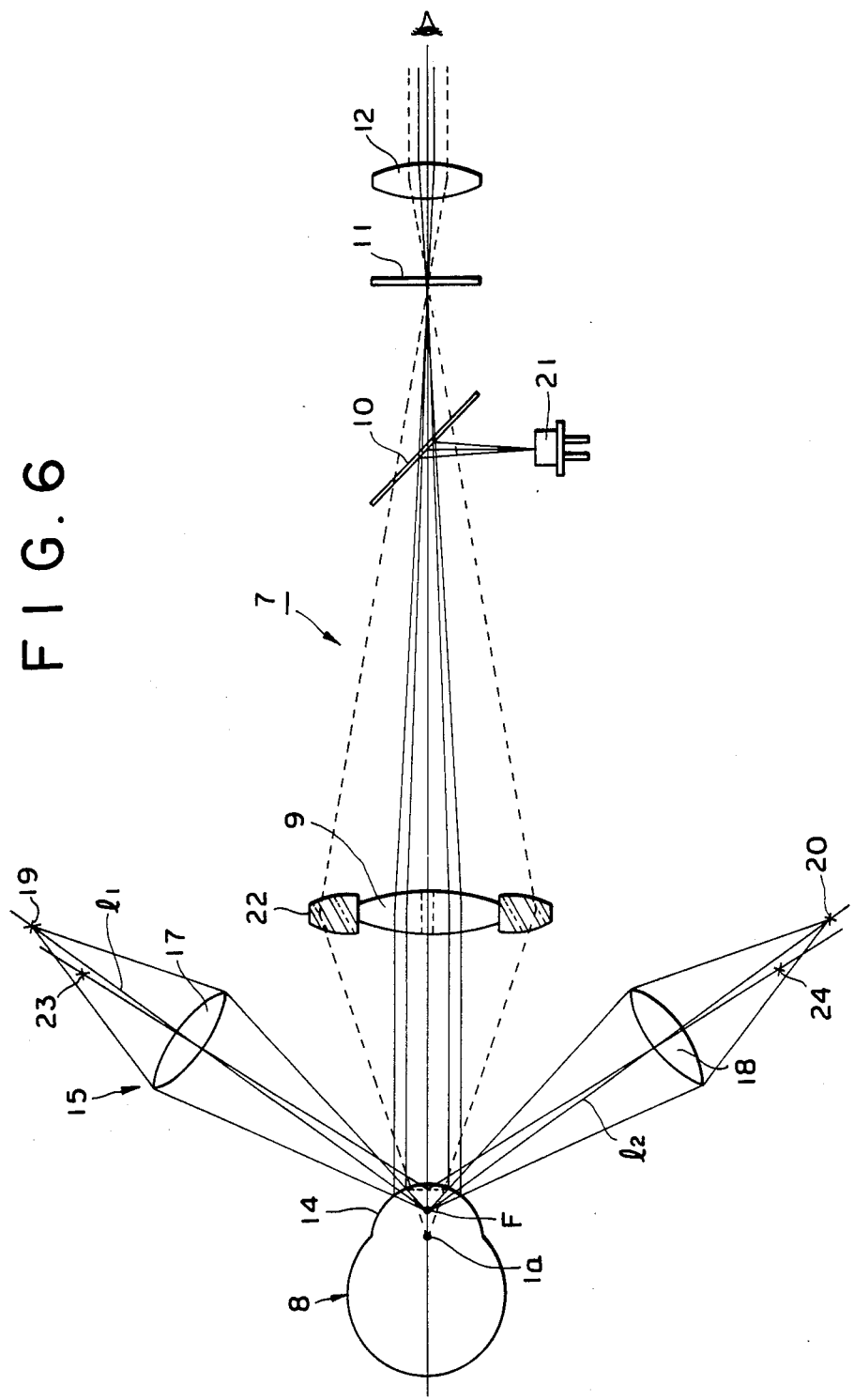
FIG. 6 is a schematic illustration of an optical system showing a non-contact type of tonometer according to a second embodiment of the present invention.

FIG. 6 illustrates a non-contact type tonometer according to a second embodiment of the present invention, wherein the objective lens 9 of the alignment verification optical system 7 is provided with the objective lens 22 for observing the anterior portion image of the retina at the outer peripheral portion thereof. According to this embodiment, the construction of the alignment verification optical system 7 is more compact when compared with the first embodiment.

Figure 7:
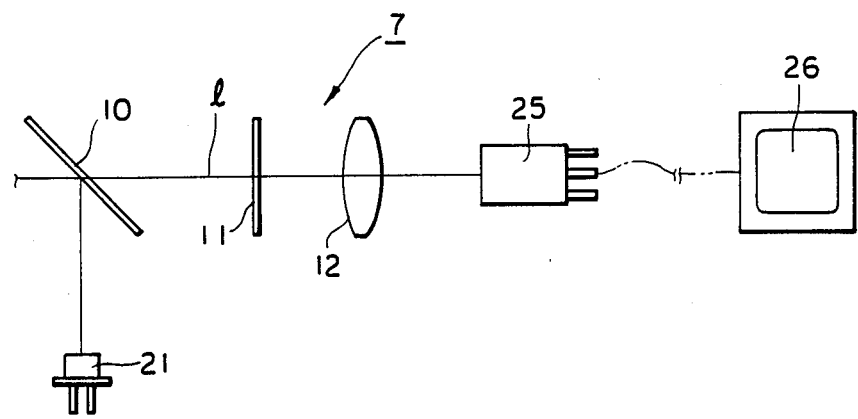
FIG. 7 is a schematic illustration for explaining a non-contact type tonometer according to a third embodiment of the present invention.
Figure 8:
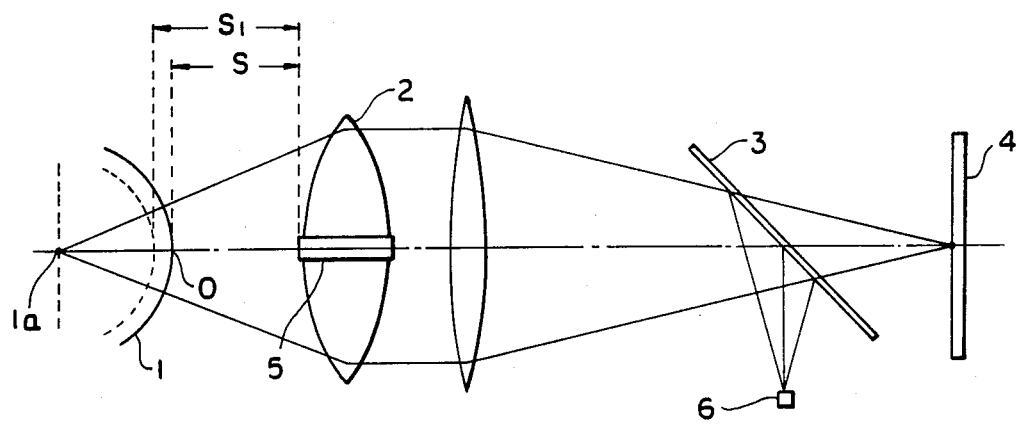
FIG. 8 is a schematic illustration for explaining an alignment verification optical system of a conventional non-contact type tonometer.

FIG. 7 illustrates a non-contact type tonometer according to a third embodiment of the present invention, wherein an image pickup tube 25 is disposed adjacent to the ocular 12 in order to display the anterior portion image and target image on a television screen.

While particular embodiments of the present embodiment have been shown in the drawings and described above, it will be apparent that many changes may be made in the form, arrangement and positioning of the various elements constituting the non-contact type tonometer. In consideration thereof, it should be understood that preferred embodiments of the present invention disclosed herein are intended to be illustrative only and are not intended to limit the scope of the present invention.

What is claimed is:

1. A non-contact type tonometer having an orifice tube for discharging a fluid to deform a cornea of an eye under test, and an alignment optical system for aligning an axis of the orifice tube with the vertex of the cornea and for indicating a predetermined working-distance between a tip of the orifice tube and the vertex of the cornea, said alignment optical system comprising:

first projection means having a first optical axis thereof for projecting a first target image on the focal point of said cornea;

second projection means having a second optical axis thereof for projecting a second target image on the focal point of said cornea;

imaging optical means having a focal point and an alignment optical axis which is coaxial with said axis of said orifice tube for forming an image of specularly reflected light rays of said first and second projecting means from said cornea, said first and second optical axes of said projection means being obliquely arranged with respect to said alignment optical axis;

means for detecting said images formed by said imaging optical means;

said first and second projection means being configured such that said first and second optical axes and said alignment optical axis intersect with each other at a first intersection point on said alignment optical axis and said first and second projection means being further adapted to form said first and second target images at said intersection point; and said tonometer being operable such that where no alignment error exists between the vertex of the cornea and the central axis of the orifice tube, and no working-distance error exists between the vertex of the cornea and the tip of the orifice tube, said first target light ray projected by said first projection means toward the cornea, and said second target light ray projected by said second projection means toward the cornea intersect at the focal point of the cornea, and a portion of the target light rays are reflected from the cornea and become parallel to said alignment optical axis of said imaging optical means, and said first and second reflected target light rays are imaged by said imaging optical means on said image detecting means and are coincident with each other at said focal point of said imaging optical means.

2. A non-contact type tonometer according to claim 1, wherein said first projection means further includes means for projecting a third target light source, disposed in a focal plane thereof, on said cornea, and said second projection means further includes means for detecting said third target light source reflected from the cornea, said third target light source of said first projection means and said detection means of said second projection means being used for detecting the deformation of the cornea.

3. A non-contact type tonometer according to claim 1, wherein said imaging optical means has first and second objective lenses, said first objective lens is configured to converge said reflected light of said first and second projection means from the cornea onto said focal point, and said second objective lens is configured to focus an iamge of an anterior portion of the eye being tested onto said image detecting means.

4. A non-contact type tonometer according to claim 3, wherein said second objective lens is disposed behind said first objective lens and has a central hole therein for passing light rays reflected by the cornea therethrough.

5. A non-contact type tonometer according to claim 4, wherein said first objective lens is disposed in said central hole of said second objective lens.

6. A non-contact type tonometer according to claim 1, wherein said means for detecting the reflected images includes a reticle plate disposed at said focal point of said imaging optical means and an ocular for observing said first and second target images projected on said reticle plate.

7. A non-contact type tonometer according to claim 1, wherein said imaging optical means includes a photoelectric imaging means, positioned at an image point of said first and second target images, for imaging said targets, and a display means for displaying said first and second targets imaged by said photoelectric imaging means.

8. A non-contact type tonometer according to claim 1, wherein said first and second optical axes are symmetrically inclined with respect to said alignment optical axis.

9. A non-contact type tonometer according to claim 8, wherein said first and second optical axes are co-planar with said alignment optical axis.

10. A non-contact type tonometer having an orifice tube for discharging a fluid to deform a cornea of an eye under test, and an alignment optical system for aligning an axis of the orifice tube with the vertex of the cornea and for indicating a predetermined working-distance between a tip of the orifice tube and the vertex of the cornea, said alignment optical system comprising:

first projection optical means, including a first projection lens having a first optical axis and a first target light source, for projecting a first target image on the cornea;

second projection optical means, including a second projection lens having a second optical axis and a second target light source, for projecting a second target image on the cornea;

imaging optical means including a first imaging lens which has a first focal point and which has an alignment optical axis coaxial with said axis of the orifice tube, and a second imaging lens, for imaging an anterior portion of the eye under test, said second lens having an optical axis coaxial with said alignment optical axis of said first imaging lens, having a central opening therein for passing light therethrough;

said first and second optical axes being symmetrically inclined and co-planar with respect to said alignment optical axis and intersecting said alignemnt optical axis at a common intersection point;

said first projection lens being configured to form said first target image at said intersection point, and said second projection lens being configured to form said second target image at said intersection point; and whereby, when no alignment error exists between the vertex of the cornea and the axis of the orifice tube, and no working-distance error exists between the vertex of the cornea and the tip of the orifice tube, said first and second target images are reflected from the cornea and become parallel to said alignment optical axis of said first imaging lens and are imaged by said first imaging lens and are coincident with each other at said focal point of said first imaging lens.

11. A non-contact type tonometer according to claim 10, wherein said first projection optical means further includes a detection light source, disposed in a focal plane of said first projection lens out of alignment with said first optical axis, for irradiating said cornea, and said second projection optical means includes a detection means, disposed in a focal plane of said second projection lens out of alignment with said second optical axis, for detecting said detection light beam reflected from the cornea to measure the deformation of the cornea when impinged by said fluid.

12. A non-contact type tonometer according to claim 10, wherein said first imaging lens is inserted in said central hole of said second imaging lens.

13. A non-contact type tonometer according to claim 10, wherein said imaging optical means includes a reticle plate disposed at said focal point of said first imaging lens, and an ocular for observing said first and second target images and said anterior eye portion image focused on said reticle plate.

14. A non-contact type tonometer according to claim 10, wherein said imaging optical means includes a photoelectric image detecting means disposed at a position conjugate to said cornea with respect to said imaging optical means, for detecting said first and second target images and said anterior eye portion image, and display means for displaying said first and second target images and said anterior eye portion image.

* * * * *